United States Patent [19]

Cassou

[11] 4,453,936

[45] Jun. 12, 1984

[54] SLEEVE FOR PROTECTION AGAINST INTERNAL CONTAMINATIONS FOR A GYNAECOLOGICAL GUN IN PARTICULAR FOR BOVINES

[75] Inventor: Robert Cassou, L'Aigle, France

[73] Assignees: Maurice Cassou; Bertrand Cassou, both of L'Aigle, France

[21] Appl. No.: 425,286

[22] Filed: Sep. 28, 1982

[30] Foreign Application Priority Data

Apr. 29, 1982 [FR] France .................... 82 07420

[51] Int. Cl.³ .......................................... A61D 1/08
[52] U.S. Cl. .................................. 604/263; 206/364
[58] Field of Search ............... 604/54, 55, 275, 263; 206/363, 364, 365, 438–440, 601–608

[56] References Cited

U.S. PATENT DOCUMENTS

| | | | |
|---|---|---|---|
| 2,616,424 | 11/1952 | Brown et al. | 604/275 X |
| 2,691,982 | 10/1954 | Jones | 604/275 X |
| 4,062,363 | 12/1977 | Bonner, Jr. | 604/54 X |
| 4,252,131 | 2/1981 | Hon et al. | 604/275 |
| 4,329,995 | 5/1982 | Anthracite | 604/54 |

FOREIGN PATENT DOCUMENTS 2450102 10/1980 France .................... 604/55

Primary Examiner—John D. Yasko
Attorney, Agent, or Firm—Fidelman, Wolffe & Waldron

[57] ABSTRACT

The invention concerns sleeves for protection against internal contaminations for a gynaecological gun for animals of the type comprising a tubular body, a chamber for storing the product to be injected or aspirated, and ejecting or aspirating means (7) operative through the front end of the body. The problem is to avoid contaminations through the medium of the gun between the vagina and the uterus of the animal.

According to the invention, such a sleeve comprises a cylindrical element (13) of flexible and thin material and having an end (13c) which is closed in a sealed manner but is tearable, the length of the sleeve approximately corresponding to the length of the whole of the gun, two substantially parallel slits (16) being provided in the vicinity of the end (13a) opposed to the closed end.

The invention is advantageous in the artificial insemination of bovines.

23 Claims, 11 Drawing Figures

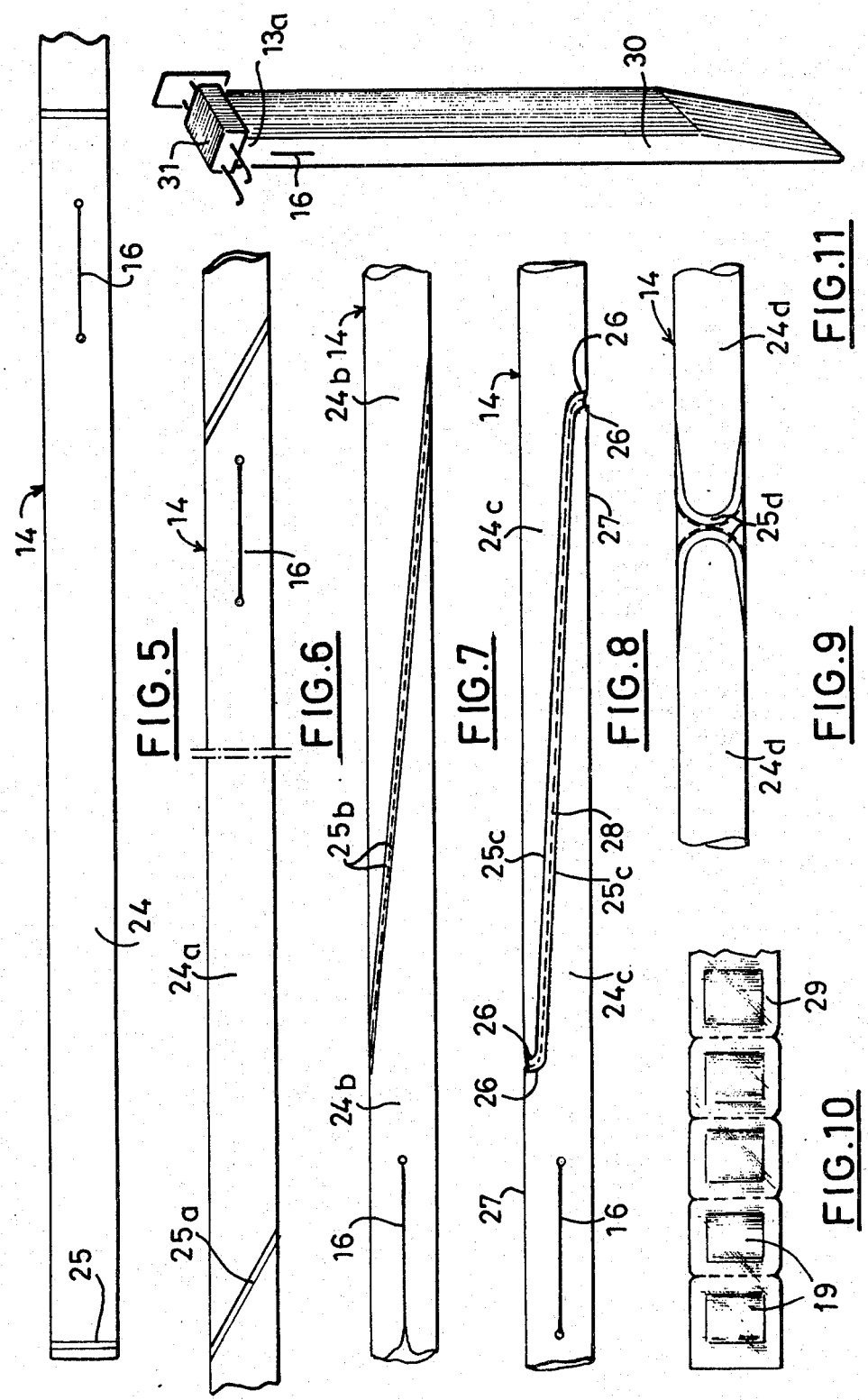

SLEEVE FOR PROTECTION AGAINST INTERNAL CONTAMINATIONS FOR A GYNAECOLOGICAL GUN IN PARTICULAR FOR BOVINES

The present invention relates to guns for gynaecological action on animals such as artificial insemination guns or guns for transferring or collecting embryos for cattle or poultry of the type comprising a tubular body, a chamber for storing the product to be injected and means for ejection through the front end of the body. This body may be completed by a semi-rigid sheath which surrounds the tubular body and is detachably secured around a holding end portion of the body. This sheath has for purpose to avoid any contact of the body of the gun itself with the animal and consequently any subsequent contamination of another animal upon a new utilization, bearing in mind that this sheath is discarded and replaced after each operation so that the gun body may remain sterile during an unlimited number of operations. Insemination guns of this type are known, in particular for bovines for example from French Pat. Nos. 1 224 918, 1 467 943, 1 525 336 or 2 358 136, in which the body is adapted to receive at its front end a reserve supply of insemination product in the form of a straw while the ejection means comprise a plunger-rod which is slidably mounted in the body adjacent to the rear end of the latter. A protective sheath is usually provided against external contaminations and extends substantially throughout the length of the body and has at its front end a convergent portion possibly comprising an inner sleeve against the interior of which bears the front end of the straw, this convergent end having of course an ejection opening facing this end. Also known, for example from French Pat. Nos. 80 04 606, 80 04 607 and 80 14 930, are guns for transferring or simply collecting embryos also for bovines, which are of the same type and in which the chamber for storing the embryos is arranged either in the form of a straw, as in the case of insemination, or in the form of an internal chamber formed in the front of the body or again (in the case of merely collecting) in the form of a separate chamber connected to the rear of the body, while, in the case of transfer, the ejection means are formed by a plunger-rod slidably mounted in the rear of the body. In the various modes of transfer there may always be provided a protective sheath against exterior contaminations, which extends either throughout the length of the body so as to act as a support for the front end of the latter, in the case of the use of a straw, or along an outer main part of the body, which is constructed telescopically, in the case of an internal storage chamber.

However, such sheaths protecting against external contaminations only effectively protect against contamination due to the passage from one animal to the following. Now, it is known that there live in the vagina, in particular in bovines, mycoplasms which are microbacteria which, if they enter the uterus, markedly reduce the rate of fecundation, above all in some geographical regions where the mycoses develop more easily. The harmful action of these mycoplasms in the uterus may occur, notwithstanding the presence of antibodies specially secreted by the uterus for combatting these mycoplasms. The protective sheath is therefore liable to transfer such mycoplasms from the vagina into the uterus. The same drawback could also arise in the case of guns having no protective sheath, for example of the disposable type (and having a non-rigid end so as to avoid injuring the animal), in which case it would be the end of the body itself which would be liable to transfer the mycoplasms from the vagina to the uterus.

The invention consequently has for object to eliminate this drawback by providing a gun of the aforementioned type whose end, which may be provided with a sheath for protecting against external contaminations (from one animal to the other) is not liable to transfer from the vagina to the uterus of the animal itself the micro-organisms which may or may not be pathogenic and may or may not be capable of developing and are formed on the walls of the vulva and of the vagina and could, if introduced in the uterus, result in harmful disorders, in particular as concerns fecundation.

This should be achieved both in the practice of artificial insemination and in the transplantation of embryos (inovulation) or in the removal of germs which develop in the mucus of the vagina. Another essential condition which must be satisfied by the solution brought to this problem by the invention, resides in the fact that this protection must require for its application the use of only one hand which holds and actuates the gun, in view of the fact that the other hand and arm are already inserted in the rectum of the animal for the purpose of feeling the wall in the vicinity of the neck of the uterus and permitting a good localization of the latter and a precise penetration of the instrument through this neck without injury.

An object of the invention is consequently to provide a sleeve for protecting against contaminations for a gun of the aforementioned type, characterized in that it is formed by a cylindrical element of flexible and thin material one end of which is closed in a sealed manner but is tearable, the length of the sleeve approximately corresponding to the length of the whole of the gun, two roughly parallel slits being provided in the vicinity of the end opposed to the closed end of the sleeve.

With this arrangement, before use, the user slips the sleeve over the body of the gun (or over its sheath if one is provided) until the end of this body (or sheath) abuts against the closed end of the sleeve, after which he inserts the assembly in the vagina of the animal by a single hand until the closed end of the sleeve, which retains the body of the gun, has started to enter the neck of the uterus, or is on the point of doing so. The user then passes the index finger of the hand holding the gun in the two slits provided in the sleeve and then pulls on the part of the sleeve which is located between these two slits and does not surround the gun so as to form, owing to the flexibility and elasticity of the material from which the sleeve is made, a semi-ring or ear, by means of which he applies to the sleeve a traction by bearing with the thumb of the same hand on the body of the gun, so that the end of the gun (or its sheath) perforates the closed end of the sleeve against which it bears. Following on this perforation, the user may insert by means of the same hand the gun inside the uterus until its end reaches the desired optimum position for the operation to be carried out. Thus, throughout the passage through the vulva and vagina, the body of the gun (or its sheath) has been completely held out of contact with the wall and therefore has been incapable of becoming contaminated by micro-organisms, while the sleeve, once perforated, stops short of the neck of the uterus. The desired protection is consequently achieved merely with the use of one and the same hand which normally holds the gun, while, moreover, the penetration in the uterus can be as deep as necessary since, owing to its flexibility, the sleeve can become wrinkled around the gun as it is moved along with the latter without limiting in any way the travel of the gun.

In a particular embodiment of the invention, it is arranged that the cylindrical element be manufactured by extrusion and be so flattened as to form two superimposed layers, the closed end of this sleeve being formed by a uniting of said layers transversely of the axis of the cylindrical element, so that these sleeves may be very easily manufactured by a simple extrusion process to which are added uniting elements, preferably thermowelding elements, and means for producing the slits. It is also possible to envisage constructing this tube by the superimposition and the continuous welding of two bands of indentical or different materials, for example associating, in the case of a band of plastics material and a band of flexible paper, the elasticity of one and the inextensibility of the other, this association guaranteeing 100% the perforation of the sleeve. In a particularly advantageous manner, each sleeve may be part of a continuous and flattened extruded tube formed by the axial juxtaposition of a series of such sleeves, this tube being axially wound in the form of a roll which is contained in a generally cylindrical charger having a slot through which the tube passes, so that the user is provided with a group of sleeves which take up a very small amount of space and are easy to dispense, the tube being unwound by merely pulling on the tube and the successive sleeves being separated by merely tearing or by means of a cutting process.

Further features and advantages of the invention will be apparent from the ensuing description of embodiments given merely by way of examples, with reference to the accompanying drawings in which:

FIGS. 5 and 6 show two different embodiments of sleeves constructed in the form of a flattened tube arranged in juxtaposed relation in the same direction;

FIGS. 7, 8 and 9 show three other embodiments in which the sleeves are arranged in the form of flattened tubes with juxtaposition of the sleeves in pairs and in head-to-toe relation;

FIG. 10 illustrates a pack in the form of a chain of rolls of the type shown in FIG. 4, and FIG. 11 illustrates the presentation of a stack of sleeves supported on pins.

Figure 1:
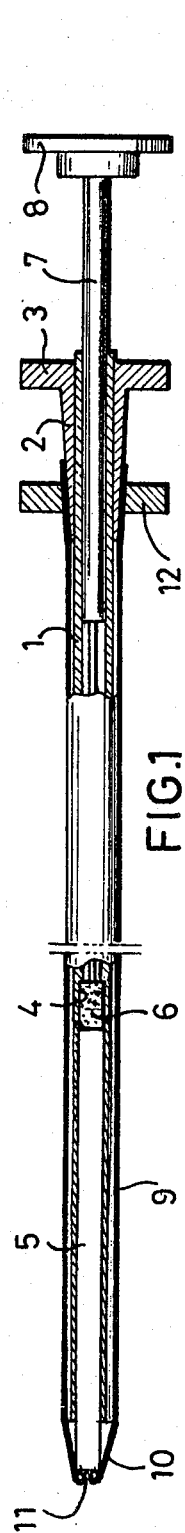
FIG. 1 is a sectional view, with a part cut away, of a gun which may be provided with a sleeve according to the invention.

The gun shown in FIG. 1 is an artificial insemination gun, in particular for bovines, which comprises a tubular body 1 provided at one end with a head 2 for fixing a sheath and terminating in an annular flange 3 for holding in the fingers. Adjacent to its other end, the body has a counterbore defining an inner shoulder 4 against which bears one end of a supply of semen or straw 5 provided with a piston-plug 6. It further comprises a plunger-rod 7 which is slidably mounted in the body 1 so as to be capable of shifting by an end thereof the piston-plug 6 and consequently ejecting the semen contained in the straw 5. At its other end, the plunger-rod 7 has a flange 8 for holding in the fingers. The body 1 and the rod 7 are for example made from stainless steel. The gun is completed by a cylindrical protective sheath 4 which covers the whole of the body 1 and the straw 5. The latter bears by its front end against the inner surface of a convergent portion 10 of this sheath which has an ejection orifice 11. At its other end, the sheath is elastically clamped against a frustoconical portion of the head 2 by means of a clamping ring 12. Such a disposable sheath 9 is employed for each insemination operation and is slipped over the gun before its insertion in the gential passages of the animal. Its front ejection end 10 can stop before reaching the neck of the uterus or even pass through this neck. This sheath is discarded once the apparatus has been withdrawn from the genital passages of the animal, so that the gun proper 1 is not soiled and may be employed without inconvenience on another animal after having been covered with another sheath.

Figure 2:
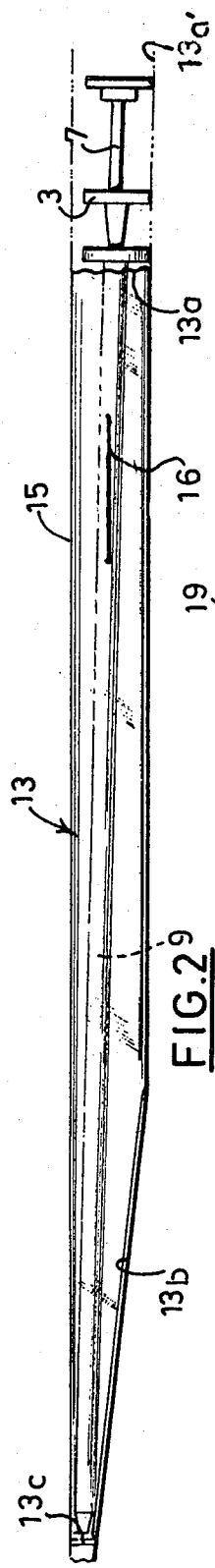
FIG. 2 is a similar outside view of the same gun provided with a sleeve according to a first embodiment of the invention.

As shown in FIG. 2, such a gun provided with its sheath 9 is enclosed in a protective sleeve 13 which is adapted to ensure that the sheath 9, in passing through the vulva and the vagina, does not gather micro-organisms which it would transfer into the uterus. This sleeve 13 is formed by a section of extruded cylindrical tube of a very flexible and thin material such as, for example, polyethylene, cellophane, biodegradable paper or a combination of these two elements, the tube being of a thickness of, for example, 25 microns. This sleeve has an end 13a which is substantially open throughout its section and through which the gun is passed into the sleeve. The opposite end 13b of the sleeve, is closed in a sealed manner. The end 10 of the sheath 9 of the gun abuts against the forwardmost part 13c of this end 13b, the length of the sleeve between this part 13c and the end 13a being such that it completely envelops the gun up to the region of the head 2 for fixing the sheath, and even beyond the flange 8 if necessary (see the end 13a' in dot-dash lines). As shown more precisely in FIG. 4, such a sleeve 13 is part of a continuous and flattened extruded tube 14 formed by the axial juxtaposition of a series of such sleeves 13. This tube, and consequently each of the sleeves, is flattened in such manner as to form two superimposed layers resting one on top of the other. The end portion 13b of each sleeve is closed in a sealed manner by uniting the two layers by thermowelding, pulse welding, ultrasounds or any other process, along a straight line which is very highly inclined, for example at 75°, relative to the transverse direction of the sleeve. This thermowelded line 13b converges with one of the two edges 15 of the flattened sleeve but does not extend to their intersection since it is interrupted by another relatively short thermowelded line which is oriented transversely of the sleeve and constitutes the forwardmost part 13c of this closed front end portion 13b. As also shown in FIG. 4, the successive sleeves 13 which form the extruded and flattened tube 14 are juxtaposed and are all disposed in the same direction, which means that the thermowelded line 13b. 13c of one sleeve is directly adjacent to the open end 13a of the following sleeve, a triangular-shaped scrap portion having been removed during manufacture between the highly inclined line 13b and the adjacent open end 13a.

Figure 4:
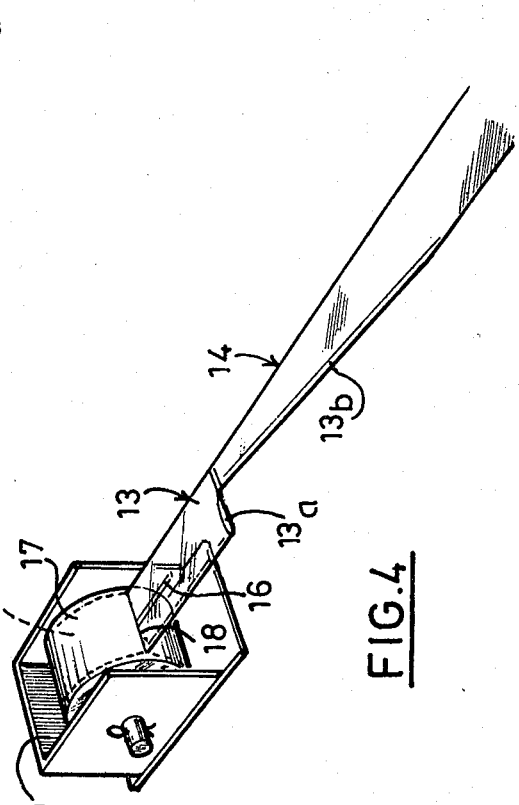
FIG. 4 represents an assembly of a series of such sleeves arranged in the form of a continuous flattened tube wound in a roll contained in a charger.
Figure 3:
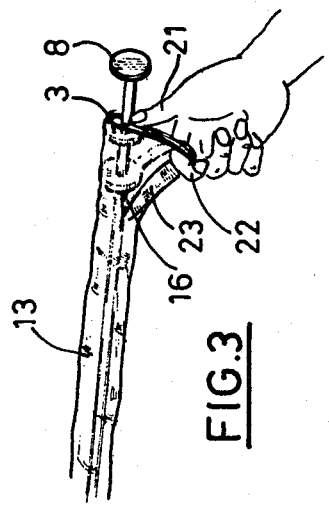
FIG. 3 illustrates the use of this gun provided with a protective sleeve according to the invention.

FIG. 4 also shows that each sleeve 13 has, in the vicinity of its open end 13a, two slits 16 which are parallel to the main axis or on the axis of the cylindrical sleeve and are even exactly superimposed when the two layers of the sleeve bear flat against each other.

The cross-section of the sleeve 13 is relatively large and may correspond to sereral times that of the gun body 1 and the protective sheath 9 covering it, so as to envelop these two elements in a relatively loose manner, even in the region of the front end where the point 10 of the sheath is surrounded with clearance by the covergent end portion which the line 13b defines with the edge 15 of the sleeve. This clearance ensures that the conical point 10 of the sheath is not "strangled" as it penetrates the sleeve before perforating the end of the latter, which movement results both in an axial elongation and a radial shrinkage which would be responsible for such a strangling. In the extreme case, the latter would result in the tearing away of a complete cone of material which would remain on the end of the sheath and would consequently enter by way of the neck of the uterus with the associated danger of entry of a foreign body and contamination which it is desired to avoid.

In the case of the particular embodiment illustrated in FIG. 2, the width of the sleeve flattened on top of the gun is of the order of three times the diameter of the latter. Further, the slits 16 are disposed approximately in the middle of the width of the flattened sleeve, as shown in FIGS. 2 and 5. Thus it is quite clear that this double arrangement enables the gun body 1 to be placed inside the sleeve 13 on one of the sides of the latter, in such manner as to be located completely on one and the same side of the assembly of the two slits 16, which will permit the easy insertion of the index finger in both if these slits as will be described hereinafter.

As also shown in FIG. 5, the tube 14 which comprises a very large number of sleeves 13 arranged in succession, e.g. of the order of several dozens of sleeves, is wound axially in the form of a roll of sleeves, termed a charge 19, placed in a charger 17 which is of generally cylindrical shape and made, for example, from plastics material or stainless steel and has a slot 18 parallel to its axis, through which slot the end portion of the wound tube 14 extends. This cylindrical charger 17 may be opened so as to receive the charge and may be placed in a distributing case, dispenser or tool case 20 that the user may place or fix as desired in a chosen place, for example on the premises or on a work case.

The protective sleeves just described are used in the following manner: With the end portion 13a of a roll of sleeves extending out of the slot 18 of the charger, the user takes hold of this portion and pulls thereon until the whole of a sleeve 13 has issued from the charger, after which he tears off or cuts this complete sleeve beyond the end thermowelding line 13c and thereby completes the opening 13a of the following sleeve. He then inserts the assembly comprising the gun 1 and the straw 5 previously covered with the sheath 9, inside this sleeve 13 by way of the end entrance opening 13a until the end 10 of the sheath abuts against the thermowelded end line 13c. In this position, the two flanges 3 and 8 of the gun and ring 12 can remain outside the sleeve 13 beyond the opening 13a, while the gun is placed on one of the sides of the sleeve so as to avoid being interposed between the two slits 16. The user then inserts the unit thus formed by the gun and the sleeve 13 in the genital passages of the animal in passing through the vulva and vagina in succession until the front end 13c of the sleeve is substantially in facing relation to the neck of the uterus, this positioning being carried out in the known manner by placing the other hand in the rectum of the animal.

By using the hand by which he placed the gun covered with its sleeve in position, the user inserts the index finger in the two slits 16 of the sleeve and, in bearing against the flange 3 of the gun with the thumb 21, he exerts by means of the index finger 22 a pull on the semi-ring or ear 23 which constitutes at this moment the part of the sleeve located on the side of the slits 16 owing to the easy plastic deformation of the material employed. This pull is exerted throughout the length of the sleeve 13 and thus acts on the thermowelded end 13c of the latter so that the covergent portion end 10 of the sheath of the gun perforates the end 13c and passes therethrough.

As this perforated end 13c is thus set back a few millimeters from the ejection orifice 11 of the sheath, the user can then cause the whole of the gun covered with the sheath 9 to travel toward the neck of the uterus until its end is placed in the desired optimum position for the insemination operation. During this penetration, the sleeve 13 wrinkles along the sheath 9 since it is retained at the rear of the neck of the uterus. Owing to this arrangement, and more particularly this unlimited possibility of wrinkling or pleating, the penetration inside the uterus may be as deep as required.

When the insemination is effected, the user withdraws the assembly and discards in succession the sleeve 13 and the sheath 9, the gun 1 being therefore unsoiled and ready for a new operation.

In the modification illustrated in FIG. 5, the closed end of each sleeve 24 which is part of an extruded tube 14, is formed by a transverse thermowelded line 25 which is perpendicular to the length of the sleeve. The slits 16 are still arranged in the same way and, when removing the first sleeve from a charger 17, the open end 13a of the sleeve had already been formed upon the separation of the preceding sleeve beyond the thermowelded line 25 of the latter.

In the modification shown in FIG. 6, the thermowelded line 25a which constitutes the closed end of the sleeve 24a is inclined at approximately 45° relative to the axis of the sleeve.

In either of the two preceding embodiments, the successive sleeves 24 or 24a pertaining to the same extruded tube 14, are all disposed in the same direction one behind the other. On the other hand, in the embodiment shown in FIG. 7, the sleeves 24b of the tube 14 are grouped in pairs in head-to-toe relation so that the two thermowelded lines 25b constituting the closed ends of the sleeves are juxtaposed. The two juxtaposed thermowelded lines 25b are disposed along straight lines highly inclined, for example at about 75°, relative to a transverse line. In this case, the successive sleeves are torn off alternatively once along the thermowelded lines 25b and then along a transverse line (not shown) along which the open ends 13a of two sleeves are juxtaposed.

In the modification shown in FIG. 8, the sleeves 24c are also grouped in pairs in head-to-toe relation, but their corresponding thermowelded lines 25c are interrupted at each of their two ends by a rounded portion 26 or a short transverse weld connected to the edge 27 of the sleeve held in the flat condition. Further, the two thermowelded lines 25c are separated by a weakening line 28 formed through the thickness of the two layers of the sleeve, for example by a succession of perforations.

In the modification shown in FIG. 9, the sleeves 24d are also grouped in pairs in head-to-toe relation and the thermowelded lines 25d have semi-circular shapes and extend throughout the width of the sleeves and are tangent to each other.

Once terminated, the roll of sleeves or charge 19 is interchangeable and these charges 19 can be packed or presented in the form of a continuous chain of successive cups 29 which are in groups, for example of one or several dozens, as shown in FIG. 10.

In a modification of the pack, the sleeves 30 may be presented in the form of a unit, i.e. not maintained in the form of a continuous tube. These various sleeves 30 constitute a stack of sleeves having the same orientation and their open ends 13a are held in position by mounting them on pins 31, as shown for example in FIG. 11.

I claim:

1. A sleeve for protecting against internal contamination for a gyneaecological gun for animals, said gun comprising a tubular body, a chamber for storing the product to be injected or aspirated and ejecting or aspirating means operative through the front end of the body, said sleeve comprising a cylindrical element of flexible and thin material having a longitudinal axis, and end which is closed in a sealed manner but is tearable, and a length approximately corresponding to the length of the whole of the gun, two substantially parallel slits being formed in the vicinity of an end of the sleeve opposed to the closed end.

2. A protective sleeve according to claim 1, wherein the cylindrical element is made by extrusion and is flattened so as to form two superimposed layers, the closed end of the sleeve being formed by uniting said layers transversely of the axis of the cylindrical element.

3. A protective sleeve according to claim 1, wherein the cylindrical element is flattened and comprises two bands of different materials welded along edges of the bands.

4. A protective sleeve according to claim 2 or 3, wherein the two slits are respectively formed in the two superimposed layers and are themselves in superimposed relation to each other.

5. A protective sleeve according to claim 1, wherein the two slits are parallel to the axis of the cylindrical element.

6. A protective sleeve according to claim 1, wherein one of two parts of the cross-section of the cylindrical element perpendicular to said axis located between the two slits corresponds to at least the cross-section of the gun.

7. A protective sleeve according to claim 2 or 3, wherein the two slits are parallel to said axis and one of two parts of the cross-section of the cylindrical element perpendicular to said axis located between the two slits corresponds to at least the cross-section of the gun, the two layers being united along a straight line perpendicular to the axis of the cylindrical element.

8. A protective sleeve according to claim 2 or 3, wherein the two slits are parallel to said axis and one of two parts of the cross-section of the cylindrical element perpendicular to said axis located between the two slits corresponds to at least the cross-section of the gun, the two layers being united along a straight line which is substantially just as inclined relative to the axis of the cylindrical element as it is relative to a transversal.

9. A protective sleeve according to claim 2 or 3, wherein the two slits are Dparallel to said axis and one of two parts of the cross-section of the cylindrical element perpendicular to said axis located between the two slits corresponds to at least the cross-section of the gun the two layers being united along a straight line which is highly inclined relative to a transversal.

10. A protective sleeve according to claim 9, wherein said straight line is rounded at each of its two ends.

11. A protective sleeve according to claim 2 or 3, wherein the two slits are parallel to said axis and one of two parts of the cross-section of the cylindrical element perpendicular to said axis located between the two slits corresponds to at least the cross-section of the gun the two layers being united along a semi-circular transverse line.

12. A protective sleeve according to claim 2, said sleeve being part of a continuous and flattened extruded tube formed by the axial juxtaposition of a series of such sleeves.

13. A protective sleeve according to claim 12, wherein the two layers are united along a straight line perpendicular to said axis, the sleeves being juxtaposed and disposed in the same direction, the uniting line of a sleeve being directly adjacent to the other end of a neighboring sleeve.

14. A protective sleeve according to claim 12, wherein the layers of each sleeve are united along a line extending transversely of the tube and the sleeves are juxtaposed and disposed in pairs in head-to-toe relation so that their uniting lines are adjacent.

15. A protective sleeve according to claim 14, wherein the uniting lines of two neighbouring sleeves disposed in head-to-toe relation are separated by a weakening line.

16. A protective sleeve according to any one of the claims 2 to 15, when the claims 5 to 15 depend from claim 2, characterized in that each uniting line claim 2 or 3, wherein said layers are united by a welded line.

17. A protective sleeve according to claim 12, wherein the continuous and flattened extruded tube is wound axially in the form of a roll contained in a charger of generally cylindrical shape and having a slot through which an end portion of said tube extends for removing each sleeve from the charger.

18. A protective sleeve according to claim 17, wherein the charger which contains the tube is itself removably mounted on a fixed dispenser.

19. A protective sleeve according to claim 17, said sleeve being part of a roll of sleeves which roll is enclosed in a chain pack arrangement:

20. A sleeve according to claim 1, wherein the two slits are located substantially on the axis of the cylindrical element.

21. A sleeve according to claim 9, wherein said straight line is interrupted by a short transverse line at each of the two ends of the straight line.

22. A sleeve according to claim 12, wherein the two layers are united along a straight line which is substantially just as inclined relative to said axis as it is relative to a transversal, the sleeves are juxtaposed and are oriented in the same direction, said uniting line of a sleeve being directly adjacent to an open end of a neighboring sleeve.

23. A sleeve according to claim 2 or 3, said sleeve being part of a stack of such sleeves which are in superimposed relation and oriented in the same direction, said stack being supported by pins at the end of the stack opposed to said closed end.

* * * * *